United States Patent [19]

Graebner

[11] Patent Number: 5,297,868
[45] Date of Patent: Mar. 29, 1994

[54] MEASURING THERMAL CONDUCTIVITY AND APPARATUS THEREFOR

[75] Inventor: John E. Graebner, New York, N.Y.

[73] Assignee: AT&T Bell Laboratories, Murray Hill, N.J.

[21] Appl. No.: 81,726

[22] Filed: Jun. 23, 1993

[51] Int. Cl.⁵ .................. G01N 25/20; G01N 25/18
[52] U.S. Cl. .................................................. 374/44
[58] Field of Search ............. 374/44, 166, 179, 43

[56] References Cited

U.S. PATENT DOCUMENTS

| | | | |
|---|---|---|---|
| 3,257,840 | 6/1966 | Skinner | 374/44 |
| 3,263,485 | 8/1966 | Mahmoodi | 374/44 |
| 3,552,185 | 1/1971 | Goode, Jr. et al. | 374/44 |
| 3,662,587 | 5/1972 | Allen et al. | 374/44 |
| 3,733,887 | 5/1973 | Stanley et al. | 374/44 |
| 4,630,938 | 12/1986 | Piorkowska-Palczewska et al. | 374/44 |
| 4,902,138 | 2/1990 | Goeldner et al. | 374/44 |
| 4,929,089 | 5/1990 | Tsuchida | 374/44 |

FOREIGN PATENT DOCUMENTS

| | | | |
|---|---|---|---|
| 0114945 | 9/1980 | Japan | 374/43 |
| 0061639 | 5/1981 | Japan | 374/44 |
| 0087850 | 7/1981 | Japan | 374/44 |
| 0935765 | 6/1982 | U.S.S.R. | 374/43 |
| 1485102 | 6/1989 | U.S.S.R. | 374/44 |
| 1557502 | 4/1990 | U.S.S.R. | 374/44 |

*Primary Examiner*—Diego F. F. Gutierrez
*Attorney, Agent, or Firm*—David I. Caplan

[57] ABSTRACT

In order to measure the in-plane thermal conductivity of a sample plate, the plate is placed in a prefabricated device containing (1) a pair of thermocouples, (2) a source of heat flow into the plate, (3) a heat sink of the heat flow having an open cavity, (4) a taut membrane, on which the source of heat flow and the thermocouples are bonded, located on the resilient filling, (5) a resilient filling of thermally insulating material located underneath the membrane, in the cavity of the heat sink, and (6) a thermally insulating medium covering the plate and exerting a compressive force on it.

19 Claims, 2 Drawing Sheets

100

300

MEASURING THERMAL CONDUCTIVITY AND APPARATUS THEREFOR

FIELD OF THE INVENTION

This invention relates to methods of, and apparatus for, measuring thermal conductivity, and more particularly measuring the thermal conductivity of thin plates such as flat diamond plates or films.

BACKGROUND OF THE INVENTION

In the case of one-dimensional steady-state heat flow through a sample body, its thermal conductivity K is given by $$K = P/A(\Delta T/\Delta x) \quad (1)$$

where P is the heat flowing per unit time along the x axis through a cross section of the body, the cross section being oriented parallel to the yz plane and having an area equal to A, and where ΔT is the temperature drop along a distance Δx measured along the x axis as can be measured by attaching to the body a pair of localized temperature sensors (thermometers), typically thermocouple junctions (thermocouples), that are spaced apart in the x direction by the distance Δx. A direct measurement technique that implements this one-dimensional heat flow is generally described in the textbook *Elementary Physics: Classical and Modern*, by Richard T. Weidner and Robert L. Sells, at pages 306–307 (1975).

In that technique, a sample body in the form of a solid circular cylinder ("rod"), having a uniform cross section A and having a pair of end surfaces, is surrounded by an insulating material, in order to minimize heat exchange into or out of the sample body through its side surfaces. One end surface of the body is maintained at a constant high temperature $T_h$, as by means of a hot reservoir or heat source, while the other end surface is maintained at a constant lower temperature $T_c$, as by means of a cold reservoir or heat sink. In the steady state, the heat crossing any cross section of the cylinder per unit time is equal to the same value P given by eq. (1) above, and the temperature gradient ΔT/Δx is the same everywhere along the rod, i.e., is independent of the x coordinate.

In prior art, implementation of this sort of one-dimensional technique has been cumbersome and time-consuming, stemming from the need for attaching the heat reservoirs and the thermometers to the sample body each time a different one is to be measured. Also, relatively lengthy and careful measurements are required to account for, and correct for, heat losses. More specifically, the required thermal insulation tends to get in the way of the thermometers (thermocouple junctions) and their wiring, as well as in the way of the heat source and its wiring—the wiring, being fine (small diameter) and fragile, and having a tendency to develop kinks and to be crunched by the required thermal insulating material.

Turning to the case of a circularly symmetric radial heat flow P, in the steady state the thermal conductivity K of a sample body is given by $$K = \frac{P \ln(R2/R1)}{2\pi h(T2 - T1)} \quad (2)$$

where T1 and T2 are the temperatures at radial distances R1 and R2 from a point on the body located at the center of circular symmetry, and where h is the thickness of the body measured parallel to its z axis, i.e., measured perpendicular to the xy plane in which the radial heat flow P is occurring. For example, the sample body was in the form of a circular cylinder having a pair of end surfaces spaced apart by h. In prior art, because of the problem of radiation and other heat losses, it was necessary that h be made much greater (by a factor of at least approximately ten) than R2 in order to ensure that the heat flow was radial. In this way, the heat flow was radial, so that K could be determined from eq. (2). However, in order to minimize errors caused by end effects, it was necessary to measure the temperatures T1 and T2 at interior points of the sample body—i.e., at points located in the midst of the sample (away from its end surfaces)—which rendered the measuring process cumbersome and time-consuming.

Moreover, the geometry of a relatively thin plate does not satisfy the aforementioned limitation on its thickness h, and therefore accurate measurements of the thermal conductivity of such a plate cannot be achieved by means of the above-described prior-art radial-heat-flow technique.

Therefore, it would be desirable to have method and apparatus for measuring the thermal conductivity of a sample body in a relatively quick and easy manner.

SUMMARY OF THE INVENTION

In order to mitigate one or more of the foregoing shortcomings of prior art, this invention involves, in one embodiment, apparatus for measuring thermal conductivity comprising:

(a) a heat sink having an open cavity;
(b) a body of thermally-insulating resilient material substantially filling the cavity;
(c) a thin membrane such as a plastic sheet located on the body of thermally-insulating resilient material;
(d) first and second spaced-apart (preferably localized) temperature sensors located on and attached to first and second spaced-apart localized portions, respectively, of the plastic sheet,
(e) a heat source located on and attached to a third localized portion of the plastic sheet;
(f) an auxiliary thermally conducting plate having a first end portion thermally attached to the heat sink and a second end portion located on a fourth localized portion of the plastic sheet, both the first and the second localized portions of the plastic sheet being located between the third and fourth localized portions thereof.

Advantageously, the plastic sheet is bonded to the heat sink, whereby the plastic sheet is maintained in a mechanically taut condition. Advantageously also, the first and second temperature sensors form a differential thermocouple, and in which access wiring to the first and second temperature sensors is bonded to the plastic sheet. Advantageously further, the apparatus further comprises a third temperature sensor located on and attached to a fifth localized portion of the plastic sheet at a location situated between the first and second localized portions thereof, the third temperature sensor having access wiring that is bonded to the plastic sheet. Advantageously also, the heat source comprises an electrical resistor bonded to the plastic sheet and having access wiring bonded to the plastic sheet.

This invention also involves, in another embodiment, a (steady-state) method of measuring the thermal conductivity of a sample body, using any of the above-described inventive apparatus, comprising the steps of:

(a) placing the sample body in a position overlying the plastic sheet and in thermal contact with the first and second temperature sensors, with the heat source, and with the thermally conducting plate; and (b) placing a thermally insulating medium covering the sample body. Advantageously further, the method further comprises the step of applying a compressive force on the thermally insulating medium, whereby the thermal resistances between the sample body and (1) the heat source, (2) the first and second spaced-apart temperature sensors, and (3) the thermally conducting plate are reduced. The thermal conductivity K can then be determined from eq. 1 or 2 (depending on the geometry) by measuring in the steady state: the relevant distances $\Delta x$ or R2 and R1 parallel to the heat flow, the cross section A or h, the temperature difference $\Delta T$ or $T2-T1$, and the power P generated by a heat source such as a resistor carrying an electrical current. If the sample body is in the form of a relatively thin plate or film—i.e., a body whose thickness is small compared with its areal dimensions—then the in-plane thermal conductivity of the plate or film is measured provided that the plate or film is laid flat on the plastic sheet.

Only for the sake of clarity, none of the drawings is to any scale.

DETAILED DESCRIPTION

Figure 1A:
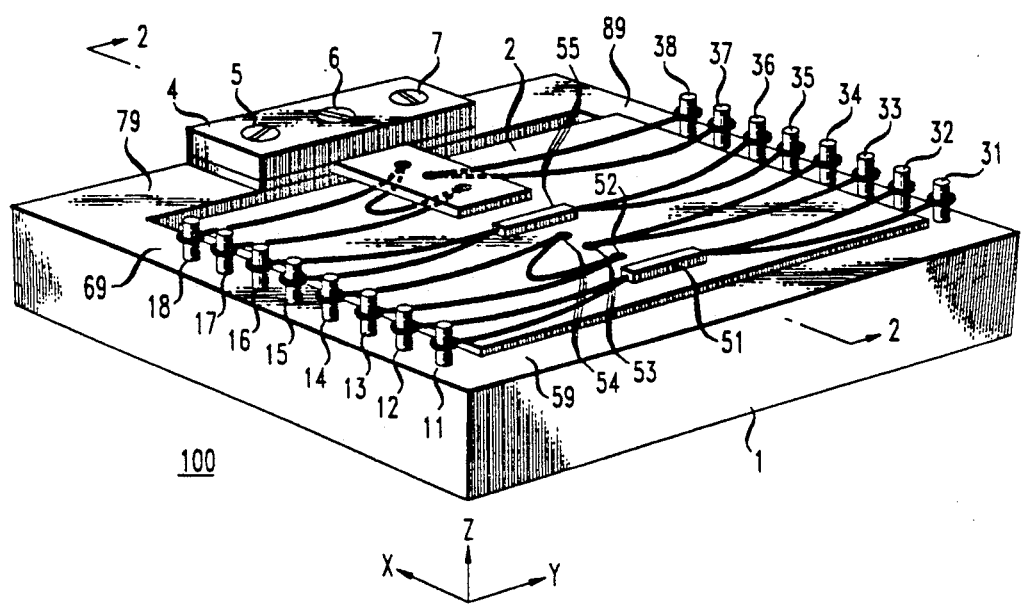
FIG. 1A is a perspective view of apparatus for measuring the thermal conductivity of sample bodies in the form of rectangular plates in accordance with a specific embodiment of the invention.
Figure 1B:
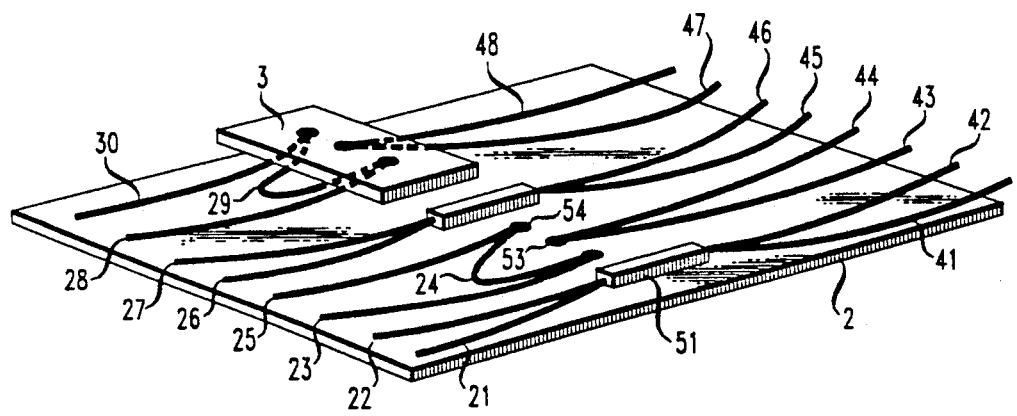
FIG. 1B is a perspective view of a portion of the apparatus shown in FIG. 1A.
Figure 2:
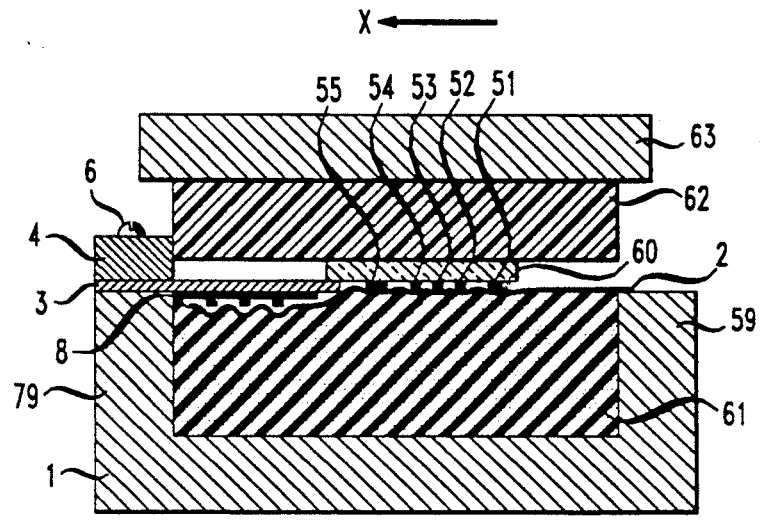
FIG. 2 is a cross-section view of an indicated section of the apparatus depicted in FIG. 1A, with a sample body in place.

As indicated in FIGS. 1A, 1B, and 2. apparatus 100 for measuring the thermal conductivity of a sample body 60 (FIG. 2) includes a heat sink 1, typically essentially of copper. This heat sink 1 typically has a square base with four walls 59, 69, 79 and 89 surrounding an open cavity. Each of these walls has a thickness that is typically in the approximate range of 1. to 2. cm, and the open cavity in the heat sink 1 is filled with a resilient filling 61 of thermally insulating material, typically foam rubber. A thin plastic sheet or membrane 2, typically of Kapton, is bonded to the top surfaces of each of the three walls 59, 69, and 89 in such a manner that the plastic sheet 2 is mechanically stretched into, and maintained in; a taut condition—i.e., the plastic sheet 2 does not sag. The plastic sheet 2 typically has a thickness of approximately 8 $\mu$m and areal dimensions of approximately 4 cm $\times$ 4 cm, and this plastic sheet 2 overlies and contacts the top surface of the filling 61.

An auxiliary thermally conducting plate 3, located overlying the left-hand portion (FIG. 2) of the thin plastic sheet 2, makes good thermal contact with the heat sink 1 by virtue of being held down firmly on a portion of the top surface of the wall 79 of the heat sink 1—such as by being firmly sandwiched between a clamping bar 4 and the top surface of the wall 79, as by means of screws 5, 6 and 7, typically brass screws.

Typically, the auxiliary thermally conducting plate 3 is essentially copper with a relatively small thickness of approximately 0.1 mm and with areal rectangular dimensions of approximately 0.5 cm $\times$ 1.0 cm. This auxiliary plate 3 is coated on its bottom surface with an electrical isolation layer 8 (FIG. 2) in case (optional) thermocouples formed by (optional) wires 28, 29, and 30 are located underneath this auxiliary plate 3, as more fully discussed below.

Binding posts 11, 12, 13, ..., 18; 31, 32, ... 38, typically essentially of copper, are bonded with electrical isolation cement, typically epoxy, into holes in the top surfaces of opposing walls 69 and 89 in such a manner that these binding posts are all electrically isolated from the heat sink 1 and hence from one another. Each of thin wires 21, 22, 23, 25, 26, 27, 28, 30, 41, 42, 43, 44, 45, 46, 47 and 48 is separately bound to a different one of these binding posts as shown in FIGS. 1A and 1B. Advantageously, each of these wires is also bonded, as by epoxy cement, to the top surface of the thin plastic sheet 2—in order to form a compact, mechanically stable wiring array located overlying the resilient filling 61. Each of the wires 21, 22, 41 and 42 typically is essentially a copper or gold wire having a diameter of approximately 25 $\mu$m—i.e., so thin that negligible amounts of heat are conducted by them.

An elongated electrical resistor 51 is attached, as by an epoxy cement, to the top surface of the thin plastic sheet 2, with one of its ends electrically connected to wires 21 and 22 and the other to wires 41 and 42.

During measurement operations, with the sample body 60 in place, voltages are applied so that an electrical current i flows from binding post 11 to binding post 31—through the wire 21, through the resistor 51, and through the wire 41. The purpose of having the additional wires 22 and 42 connected at each end of the resistor 51 is to provide zero-current-carrying wires—in order to enable a more accurate measurement of the voltage developed across the resistor 51, as this voltage is required for the calculation of P in eq. (1).

The wires 23 and 25, together with a wire 24, form a differential thermocouple by virtue of thermocouples formed at junctions 52 and 54, whereas the wire 43 and 44 form a single thermocouple at junction 53. Typically, the wires 23 and 25 are essentially Chromel or Constantan, while the wire 24 is essentially Constantan or Chromel, respectively, each having a typical diameter of approximately 50 $\mu$m. As known in the art, the voltage $\Delta V$ developed and measured across the binding posts 13 and 14 is, then proportional to the temperature difference $\Delta T$ between the junctions 52 and 54, whereby the value $\Delta T/\Delta x$ needed for eq. (1) can be determined from a measurement of the distance $\Delta x$ between these junctions 52 and 54.

The wires 43 and 44 form the thermocouple junction 53. Typically, one of these wires is Chromel and the other is Constantan, whereby the voltage V developed and measured across the binding posts 33 and 34 is proportional in known manner to the absolute temperature at the junction 53—the binding posts 33 and 34 both being at the same absolute temperature as the known temperature of the heat sink 1. Advantageously, this junction 53 is located approximately midway between the junctions 52 and 54, in order to calibrate the voltage ΔV measured across the binding posts 13 and 14—i.e., to enable conversion of this voltage ΔV into the desired temperature difference ΔT.

Advantageously, the distance between the resistor 51 and the thermocouple junction 52 is at least ten times the thickness of the sample body 60, so that the distribution of directions of the heat flow through this sample body 60 is independent of position along the x direction (from the resistor 60 toward the auxiliary plate 3) at least in the regions near and between the thermocouple junctions 52, 53 and 54. The connection of the left-hand end of the sample body 60 to the auxiliary plate 3 advantageously is such that a local thermal conductance is achieved that is uniform across the width of the sample (unless the length of the sample in the x direction is much greater than its width as well as its thickness).

Optionally, another resistor 55—together with wires 26, 27, 45 and 46, and binding posts 15, 16, 35 and 36—can be added for the purpose of determining a correction due to loss of heat by conduction or by radiation, or by both, from the surface of the sample body 60, as more fully explained in a paper by J. E. Graebner and J. A. Herb entitled "Dominance of Intrinsic Phonon Scattering in CVD Diamond", published in *Diamond Films and Technology*, Vol. 1, No. 3, pp. 155-164 at pp. 157-158 (1992). Also, optionally another differential thermocouple—formed by junctions between (e.g., Chromel and Constantan) wires 28 and 29 (respectively), and by (e.g., Constantan and Chromel, respectively) wires 29 and 30 (respectively)—can be added, together with another thermocouple formed by (e.g., Constantan and Chromel) wires 47 and 48 (respectively) for the purpose of checking for loose or otherwise poor thermal connection between the auxiliary plate 3 and the heat sink 1 or between the auxiliary plate 3 and the sample body 60.

Advantageously, the sample body 60 is in the form of a rectangular plate having a uniform thickness that is much smaller that the length or width of the plate. The plate need not be rectangular provided that the width (in the y direction) of its right-hand end is approximately equal to the length of the resistor 51 (also in the y direction) and that the width of its left-hand end is approximately equal to the width of the auxiliary plate 3, and provided that the width of the plate (in the y direction) is uniform in the region between the thermocouple junctions 52 and 54—all in order to assure one-dimensional flow of heat between these thermocouple junctions 52 and 54. The apparatus 100 is thus adapted for measuring the in-plane (xy plane) thermal conductivity of the sample body 60 in its x direction.

The purpose of the plastic sheet 2 is to enable prefabrication of a stable mechanical support system for such elements as the resistor 51 and the thermocouple junctions 52, 53, and 54, together with their access wires 21, 22, 23, 24, 25, 41, 42, 43, and 44. The thermocouple junctions such as junctions 52, 53, and 54 typically are all formed by spot-welding in an arc, or by soldering with a lead-tin solder in an acid-containing flux.

During operations for measuring the (in-plane) thermal conductivity (in the x direction) of the sample body 60, the body 60 is positioned with its left-hand end overlying the auxiliary plate 3 and with its right-hand end overlying the resistor 51. After thus positioning the sample body 60, a thermally insulating medium 62, such as styrofoam, is placed overlying the sample body 60, the remaining (exposed) top surface portion of the plastic sheet 2, and the top surface of the auxiliary plate 3. By virtue of a compressive force, typically produced by a metallic weight 63, the thermally insulating medium 62 is urged downward, whereby the distances of separation between the bottom of this medium 62 and the exposed top surface portion of the plastic sheet 2 and the auxiliary plate 3 are reduced. In this way, undesired heat loss is reduced and good thermal contact is achieved between the sample body 60 and the heaters, the thermocouple junctions, and the auxiliary plate 3.

Also, during these operations for measuring the in-plane thermal conductivity of the sample body 60, the resistor 51 serves as a heating element or heat (power) source by virtue of a current i driven through it by a current source (not shown) connected to the binding posts 11 and 31. After a steady state is obtained (i.e., the readings of the thermocouples do not change with the passage of time), the value of P in eq. (1) is thus equal to $P = vi$, where $v$ is measured voltage drop across the resistor 51, as measured across binding posts 12 and 32, and where i is the above-mentioned current flowing through the resistor 51, via the binding post 11 and the binding post 31, as measured by known techniques. The foregoing equation $P = vi$ is valid provided that all or substantially all of the heat generated by the resistor 51, and no other heat, enters the sample body 60, and provided that the only heat that exits the sample body 60 does so at regions located to the left-hand side of a thermocouple junction 54 to be described more fully below. These provisos are satisfied by virtue, among other things, of the thermal insulation supplied by the filling 61 and the medium 62, provided the width (in the y direction) of the sample body 60 is significantly less than both that of the filling 61 and that of the medium 62.

Since $P = vi$ can thus be calculated from the measured values of $v$ and i, and since the value of $\Delta T/\Delta x$ can be determined from the thermocouple voltage measurements as discussed above, and since the cross-sectional area A of the sample body 60 can be measured by known techniques, the desired value of the in-plane thermal conductivity of the sample body 60 in the x direction can then be calculated from eq. (1)—after a steady state (thermal equilibrium) has been established, and thus after the measured values of ΔT, and hence after the values of K calculated from eq. (1) do not vary with time. Using the apparatus 100, the in-plane thermal conductivities in the x direction of different sample bodies, one after another, can thus be measured as described above for a single sample body, simply by removing the weight 63 and the medium 62 after measuring the thermal conductivity of each sample body and then proceeding with the next sample body as described above.

Figure 3:
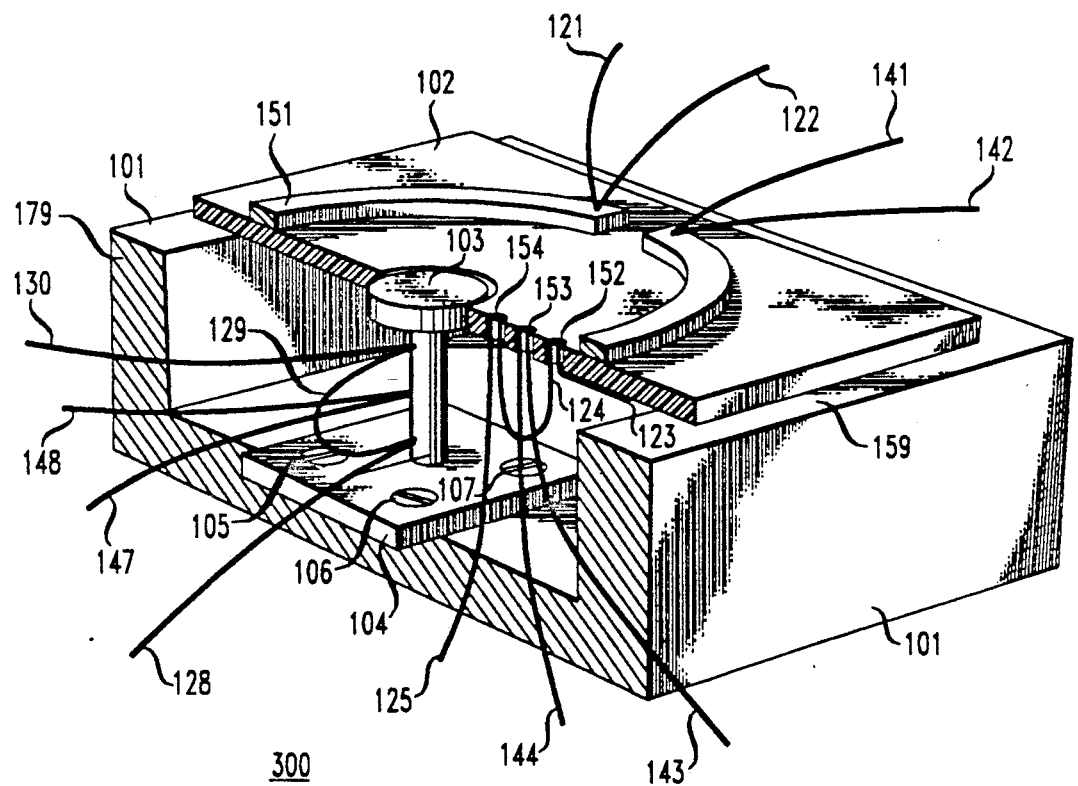
FIG. 3 is a cut-away perspective view of apparatus for measuring the thermal conductivity of plates, in accordance with another specific embodiment of the invention.

FIG. 3 depicts apparatus 300 that can be used for measuring thermal conductivity in case the sample body (not shown only for purposes of clarity and visibility) has irregularly-shaped outer contours. Elements depicted in FIG. 3 that are similar in structure and function to those depicted in FIGS. 1 and 2 are denoted by the same reference numbers plus 100. The cavity in the heat sink 101 is filled with a resilient filling (not shown) similar to the above-described filling 61. The major difference between FIG. 3 and FIGS. 1A, 1B, and 2 is that the heating element 151 is circular rather than linear, and that the auxiliary plate 3 (FIGS. 1A, 1B, and 2) becomes a pedestal 103 (FIG. 3).

The wires 121, 122, 141, and 142 are bonded (not shown only for the sake of clarity and visibility), typically with an epoxy cement, to the top surface of the plastic sheet 102; the wires 123, 124, and 125 are similarly bonded (not shown only for the sake of clarity and visibility) to the bottom surface of the plastic sheet 102; and the wires 128, 130, 147, and 148 are similarly bonded to the side surfaces of the pedestal of the pedestal 103 (rather than dangling in space as shown in FIG. 3 only for the sake of clarity and visibility). During measurements of thermal conductivity, the sample body (not shown) is placed overlying the heating element or resistor 151 so that the sample body covers all points thereof and everywhere extends beyond it, in order to achieve circularly symmetric heating of the sample body. During operation with the apparatus 300, a thermally insulating medium (not shown in FIG. 3) analogous to the medium 62 is placed overlying the sample body, and a weight analogous to the weight 63 is placed overlying this thermally insulating medium. The in-plane (xy) thermal conductivity is then calculated using eq. (2).

It is advantageous that a thermally conducting grease is put on the underside of the sample body prior to placing the sample body into the apparatus 100 or 300, in order to improve thermal contact of the sample body with the thermocouple junction, as well as with the resistor and the auxiliary plate 3 or the pedestal 103. It is also advantageous that operations (when measurements are being made) be performed while the apparatus 100 or 300 is located in an evacuated chamber, typically at a pressure of approximately 1 Pascal or less.

Although the invention has been described in terms of specific embodiments, various modifications can be made without departing from the scope of the invention. For example, the wires (e.g., 21, 22, ..., 30; 41, 42, ..., 121, 122, 123, 124, 125, 141, 142, 143, 144) and the resistors (e.g., 51, 55, 151) can be formed on the plastic sheet (e.g., 2, 102) by depositing them as thin-film wires and resistors, respectively.

I claim:

1. Apparatus for measuring thermal conductivity comprising:
   (a) a heat sink body having an open cavity;
   (b) a body of thermally-insulating resilient material substantially filling the cavity;
   (c) a thin membrane located on an exposed portion of the body of thermally-insulating resilient material;
   (d) first and second spaced-apart temperature sensors located on, and attached to, first and second spaced-apart localized portions, respectively, of the thin membrane;
   (e) a heat source located on and attached to a third localized portion of the thin membrane; and
   (f) an auxiliary thermally conducting plate having a first end portion thermally attached to the heat sink body and a second end portion located on a fourth localized portion of the thin membrane, both the first and the second localized portions of the thin membrane being located between the third and fourth localized portions thereof.

2. Apparatus according to claim 1 in which the thin membrane is a plastic sheet that is bonded to the heat sink body, whereby the plastic sheet is maintained in a mechanically taut condition.

3. Apparatus according to claim 1 in which the first and second temperature sensors from a differential thermocouple, and in which access wiring to the first and second temperature sensors is bonded to the thin membrane.

4. Apparatus according to claim 3 further comprising a third temperature sensor located on and attached to a fifth localized portion of the thin membrane at a location situated between the first and second localized portions thereof, the third temperature sensor having access wiring that is bonded to the thin membrane.

5. Apparatus according to claim 1 in which the heat source comprises an electrical resistor that is bonded to the thin membrane and in which access wiring is bonded to the thin membrane.

6. A method of measuring the thermal conductivity of a sample body including the steps of:
   (a) providing an apparatus comprising:
      (1) a heat sink body having an open cavity,
      (2) a body of thermally-insulating resilient material substantially filling the cavity,
      (3) a thin membrane located on an exposed portion of the body of thermally-insulating resilient material,
      (4) first and second spaced-apart temperature sensors located on, and attached to, first and second spaced-apart localized portions, respectively, of the thin membrane,
      (5) a heat source located on and attached to a third localized portion of the thin membrane, and
      (6) an auxiliary thermally conducting plate having a first end portion thermally attached to the heat sink body and a second end portion located on a fourth localized portion of the thin membrane, both the first and the second localized portions of the thin membrane being located between the third and fourth localized portions thereof;
   (b) placing the sample body in a position overlying the thin membrane and in thermal contact with the first and second temperature sensors, with the heat source, and with the auxiliary plate; and
   (c) placing a thermally insulating medium on the sample body.

7. The method of claim 6 further comprising the step of applying a compressive force on the thermally insulating medium, whereby the thermal resistance between the sample body and the heat source, the thermal resistance between the sample body and the first and second spaced-apart temperature sensors, and the thermal resistance between the sample body and the auxiliary plate are reduced.

8. The method of claim 7 in which the thin membrane is a plastic sheet that is bonded to the heat sink body, whereby the plastic sheet is maintained in a mechanically taut condition.

9. The method of claim 6 in which the thin membrane is a plastic sheet that is bonded to the heat sink body, whereby the plastic sheet is maintained in a mechanically taut condition.

10. The method of claim 9 further comprising the step of applying a compressive force on the thermally insulating medium, whereby the thermal resistance between the sample body and the heat source, the thermal resistance between the sample body and the first and second spaced-apart temperature sensors, and the thermal resistance between the sample body and the auxiliary plate are reduced.

11. The method of claim 6 in which the first and second temperature sensors form a differential thermocouple, and in which access wiring to the first and second temperature sensors is bonded to the thin membrane.

12. The method of claim 11 further comprising the step of applying a compressive force on the thermally insulating medium, whereby the thermal resistance between the sample body and the heat source, the thermal resistance between the sample body and the first and second spaced-apart temperature sensors, and the thermal resistance between the sample body and the auxiliary plate are reduced.

13. The method of claim 11 in which the thin membrane is a plastic sheet that is bonded to the heat sink body, whereby the plastic sheet is maintained in a mechanically taut condition.

14. The method of claim 6 in which step (a) thereof further comprises providing a third temperature sensor located on and attached to a fifth localized portion of the thin membrane at a location situated between the first and second localized portions thereof, the third temperature sensor having access wiring that is bonded to the thin membrane.

15. The method of claim 14 further comprising the step of applying a compressive force on the thermally insulating medium, whereby the thermal resistance between the sample body and the heat source, the thermal resistance between the sample body and the first and second spaced-apart temperature sensors, and the thermal resistance between the sample body and the auxiliary plate are reduced.

16. The method of claim 14 in which the thin membrane is a plastic sheet that is bonded to the heat sink body, whereby the plastic sheet is maintained in a mechanically taut condition.

17. The method of claim 6 in which the heat source comprises an electrical resistor that is bonded to the thin membrane and in which access wiring is bonded to the thin membrane.

18. The method of claim 17 further comprising the step of applying a compressive force on the thermally insulating medium, whereby the thermal resistance between the sample body and the heat source, the thermal resistance between the sample body and the first and second spaced-apart temperature sensors, and the thermal resistance between the sample body and the auxiliary plate are reduced.

19. The method of claim 17 in which the thin membrane is a plastic sheet that is bonded to the heat sink body, whereby the plastic sheet is maintained in a mechanically taut condition.

* * * * *